United States Patent [19]
Klein et al.

[11] Patent Number: 5,001,049
[45] Date of Patent: Mar. 19, 1991

[54] METHOD FOR DETERMINATION OF HIV SPECIFIC ANTIBODIES

[75] Inventors: Christian Klein; Hubert Bayer, both of Weilheim, Fed. Rep. of Germany

[73] Assignee: Boehringer Mannheim GmbH, Mannheim, Fed. Rep. of Germany

[21] Appl. No.: 467,602

[22] Filed: Jan. 19, 1990

[30] Foreign Application Priority Data

Jan. 23, 1989 [DE] Fed. Rep. of Germany ....... 3901857

[51] Int. Cl.$^5$ .................. C12Q 1/70; A61K 37/02; C07K 7/00
[52] U.S. Cl. ........................ 435/5; 530/317; 530/329; 435/7.5; 435/974
[58] Field of Search ............... 435/7, 5; 530/317, 329

[56] References Cited

U.S. PATENT DOCUMENTS 4,746,604  5/1988  Mowshowitz ................. 435/7

FOREIGN PATENT DOCUMENTS 0326490  6/1989  European Pat. Off. .

OTHER PUBLICATIONS

Gnann, J. W. Science, 237: 1346–1349.

Primary Examiner—Robert A. Wax
Assistant Examiner—Bradley L. Sisson
Attorney, Agent, or Firm—Felfe & Lynch

[57] ABSTRACT

The invention relates to a method for determining HIV (human immunodeficiency virus) specific antibodies. A sample is incubated with a solid phase, to which streptavidin is bound in a way to make 0.1–2.5 μg streptavidin per ml of reaction volume available for binding, a biotinylated polypeptide, and a labelled receptor which binds to HIV specific antibodies. The biotinylated polypeptide contains at least one of the amino acid sequences $\overline{\text{CAFROVC}}$ and $\overline{\text{CSGKLIC}}$, and is from 7 to 50 amino acids long. Following complex formation onto the solid phase, solid and liquid phase are separated, and label is measured in one of these.

17 Claims, No Drawings

METHOD FOR DETERMINATION OF HIV SPECIFIC ANTIBODIES

FIELD OF THE INVENTION

The invention concerns a method for the determination of antibodies to HIV and a suitable reagent therefor.

BACKGROUND OF THE INVENTION

The determination of HIV antibodies is an important diagnostic task.

Peptide sequences taught in WO 88/08005 and Science 237 (1987), 1346–1349, can be used to detect antibodies to HIV-2, using immunoassays. In the methods of determination described therein, synthetic peptides have to be used in high concentrations and only small signals are obtained with high blank values.

The abstract "DEVELOPMENT OF HIV-1 AND HIV-2 SPECIFIC AND SELECTIVE ENZYME LINKED IMMUNOSORBENT ASSAY BASED ON TRIPALMITOYL-S-GLYCERYL-CYSTEINYL-PEPTIDES" from the 20th EUROPEAN PEPTIDE SYMPOSIUM, Sept. 4–9, 1988 in Tübingen/FRG teaches that the sensitivity of an HIV-2 assay can be improved by cyclization of a HIV-2 peptide, via two cysteine residues contained therein. However, the Pam₃Cys-peptide conjugate described therein is not completely suitable for a sensitive HIV-2 test. Large amounts of the conjugate are necessary in order to immobilize the antibodies, and high blank values still result, even though the sensitivity is improved.

Cyclic HIV-2 and HIV-1 peptides are also known from EP-A 0 326 490. These peptides also have to be used in large amounts for immunological tests and the results also show very high blank values.

The object of the present invention is therefore to provide a method for the determination of HIV antibodies with which these disadvantages can be eliminated.

SUMMARY OF THE INVENTION

The object of the invention is to provide a method for the determination of HIV antibodies wherein the sample is incubated, either simultaneously or sequentially, in a reaction vessel on the inner surface of which streptavidin is bound in such an amount that 0.1 µg - 2.5 µg are available per ml reaction volume, with:

(a) at least one biotinylated polypeptide which consists of a maximum of 50 amino acid residues and contains the amino acid sequence $$\overline{\text{CAFRQVC}} \text{ and/or } \overline{\text{CSGKLIC}},$$

wherein the two cysteines of each sequence are cyclized to form intramolecular cystine bridges, and (b) a labelled receptor which specifically binds to HIV specific antibodies, separating liquid and solid phase and determining the label in one of the two phases as a measure of the HIV antibody.

In determining the HIV-2 antibodies a biotinylated polypeptide which contains the amino acid sequence $$\overline{\text{CAFRQVC}}$$

is preferred.

DETAILED DESCRIPTION OF PREFERRED EMBODIMENTS

Surprisingly, it has been found that by using a streptavidin containing solid phase in combination with biotinylated monomeric, cyclic HIV peptides, high sensitivity is obtained with low blank values, using small amounts of the peptides.

The streptavidin solid phase is described in EP-A 0 344 578 which corresponds to co-pending U.S. application Ser. No. 356,336, the disclosure of which is incorporated by reference herein and its contents are an object of the present application.

Suitable polypeptide sequences are described in WO 88/08005, U.S. Pat. No. 4,812,556, EP-A 0 283 327 and EP-A 0 326 490. The sequences cited therein can be used according to the present invention after biotinylation, cyclization and isolation of the biotinylated monomeric cyclic peptides. Biotinylated peptides which are particularly suitable are compounds of the formula:

$$X-U-\overline{\text{NSWGCAFRQVCHTT}} \text{ or}$$

$$\overline{\text{NSWGCAFRQVCH}}-B-J,$$

in which

X is a biotinylaminocaproic acid, biotinylaminobutyric acid, biotinyl, N-epsilonbiotinyllysine, N-epsilon(biotinyaminocaproyl)lysine, N-deltabiotinylornithine or N-delta(biotinylaminocaproyl)ornithine residue;

J is a N-epsilon-biotinyllysine, N-epsilon(biotinylaminocaproyl)lysine, N-delta-biotinylornithine or N-delta-(biotinylaminocaproyl)-ornithine residue;

U is a bond, the amino acid I„ or a peptide sequence selected from the group consisting of QARL, ARL, and RL;

B is a bond, the amino acid T, or a peptide sequence selected from the group consisting of TTVPW, TTVP, TTV, and TT.

Biotinylated peptides which are equally suitable are compounds of the formula:

$$X-O-\overline{\text{GCSGKLICTT}}-Z \text{ or}$$
$$O-\overline{\text{GCSGKLICTT}}-Z-J$$

in which

O is a bond, the amino acid W, or a peptide sequence KDQQLLGIW, DQQLLGIW, QQLLGIW, QLLGIW, LLGIW, LGIW, GIW, or IW;

Z is a bond, the amino acid A, or a peptide sequence selected from the group consisting of AVPWNAS, AVPWNA, AVPWN, AVPW, AVP, or AV, and X and J have the meaning mentioned above.

It is preferred to use a mixture of biotinylated polypeptides for the simultaneous determination of HIV-1 and HIV-2, wherein the first polypeptide contains the amino acid sequence

CAFRQVC
|_____| and the second polypeptide contains the amino acid sequence

CSGKLIC.
|_____|

It is also preferred to use a peptide which contains both amino acid sequences.

The preparation of the biotinylated peptides be carried out e.g., according to Merrifield JACS 85 (1964), 2146. Biotinylation can be carried out e.g., by following PNAS 80 (1983), 4045. The peptides are cyclized before or after biotinylation by oxidation and the monomer is isolated by chromatography, preferably HPLC chromatography.

The preparation of the peptides can be carried out by first synthesizing the corresponding peptide sequences, followed by oxidation of the cysteine-SH groups to form cyclized cystine peptides and then by subsequent biotinylation with a biotinylating agent, for example, biotinyl-aminocaproic acid-N-hydroxysuccinimide ester. Alternately, the peptides may first be biotinylated and then cyclized by oxidation.

The peptides can be prepared, e.g., by solid phase synthesis, with, e.g. temporary tert. butyloxycarbonyl protection of the alpha amino acids (Merrifield, JACS 85 (1964), 2146) or with temporary fluorenyl-methoxycarbonyl protection ("Fmoc") (Meienhofer, Int. J. Pept. Prot. Res 11 (1978), 246).

A further way to prepare the peptides used in the present invention is to introduce the biotin residue during solid phase synthesis using, e.g., N-alpha-Fmoc-N-epsilon-(biotinylaminocaproyl)lysine, N-alpha-Fmoc-N-epsilon-biotinyllysine or, in the case of biotinylation the N-terminal amino acid, biotin-N-hydroxysuccinimide ester or biotinylaminocaproic acid-N-hydroxysuccinimide ester. A particularly preferred method of production involves cyclization of the peptides while they still on the polymer carrier after solid phase synthesis. For this, cysteine protected at the SH-group by a trityl residue is used and the peptides bound to the solid phase are treated with iodine in a solvent mixture which contains a perfluorinated compound, preferably dichloromethane/hexafluoroisopropanol. Using this method, monomeric peptides are almost exclusively obtained and practically no polymers.

The biotinylated monomeric peptides are preferably used
in a concentration of from about 0.005 μg/ml to about 0.4 μg/ml. An especially preferred concentration is one of from about 0.02 μg/ml to about 0.3 μg/ml. The length of the peptides is a maximum of 50 amino acids. A preferred embodiment uses a maximum of 35 amino acids and a particularly preferred embodiment uses a maximum of 20 amino acids.

An antibody which is directed against the Fcγ part of human immunoglobulin is preferably used as the labelled receptor. This antibody can be monoclonal as well as polyclonal. Especially preferred is an antibody which is directed against the Fcγ part of human IgG.

Labels familiar to the expert, including for example enzymes (e.g. peroxidase, alkaline phosphatase), radionucleotides, fluorogenic or chromogenic substrates, cofactors, colloidal gold or magnetic particles, can be used.

The method according to the present invention is carried out in such a way that the sample and biotinylated, antigen are added to a streptavidin containing solid phase simultaneously, incubated and washed. Afterwards labelled antibody to HIV-1 and/or HIV-2 antibody is added, incubated, washed and the label is determined in the solid phase or the liquid phase which has been separated. Such a proceeding is preferred but it is also possible to add the sample, biotinylated antigen and—without a preceding washing step—labelled antibody to HIV-1 and/or HIV-2 antibody to a streptavidin containing solid phase and to determine after washing the label in the solid phase or the liquid phase.

A variant of the determination procedure is based on the use of labelled polypeptides as labelled receptors which consist of a maximum of 50 amino acid residues and which contain the amino acid sequence CAFRQVC and/or CSGKLIC preferably CAFRZVC, whereby in each case both cysteines (C) of these amino acid sequences are cyclized to cystine bridges and the polypeptide is monomeric. Preferred are polypeptides of the formula:

X—U—NSWGCAFRQVCHTT or

NSWGCAFRQVCH—B—J
|_____| in which
X is a biotinylaminocaproic acid, biotinylaminobutyric acid, biotinyl N-epsilon-biotinyllysine, N-epsilon(biotinyaminocaproyl)lysine, N-delta-biotinylornithine or N-delta(biotinylaminocaproyl)-ornithine residue;
J is a N-epsilon biotinyllysine, N-epsilon(biotinylaminocaproyl)lysine, N-delta-biotinylornithine or N-deltabiotinylaminocaproyl)-ornithine residue;
U is a bond, L, or a peptide sequence selected from the group consisting of QARL, ARL and RL,
B is a bond, T or a peptide sequence selected from the group consisting of TTVPW, TTVP, TTV and TT,
Biotinylated peptides which are equally suitable are compounds of the formula:

X—O—GCSGKLICTT—Z or

O—GCSGKLICTT—Z—J in which
O is a bond, W, KDQQLLGIW, DQQLLGIW, QQLLGIW, QLLGIW, LLGIW, LGIW, GIW, or IW,
Z is a bond, A, AVPWNAS, AVPWNA, AVPWN, AVPW, AVP, AV, and X and Y have the meaning mentioned above.

The following examples elucidate the invention further.

EXAMPLE 1

Synthesis of biotinylaminocaproyl $\overline{\text{NSWGCAFRQVCHTT}},$ monomeric, cyclic.

The peptide AsnSer(tBu)TrpGlyCys(Trt)AlaPheArg(Mtr)GlnValCys(Trt)His(Trt)Thr(tBu)Thr(-tBu)is synthesized on the solid phase following Meienhofer supra. Afterwards, the peptide resin is shaken for 2 hours in a 100 fold volume of dichloromethane/hexafluoroisopropanol (3:1) saturated with iodine and washed three times with each of dichloromethane, dimethylformamide and isopropanol. Afterwards, the peptide is cleaved from the resin as described by Meienhofer, biotinylated with biotinylaminocaproic acid-N-hydroxysuccinimide ester and purified by preparative HPLC.

FAB—MS (positive): MH+ = 1947.

After cleavage with dithiothreitol the retention time in the HPLC is increased (reversed phase RP 18, gradient 0.1% trifluoroacetic acid in water against 0.1% trifluoroacetic acid in water/acetonitrile 40:60).

EXAMPLE 2

Method for the determination of HIV-2 antibodies

HIV-2 antibodies are determined in a 2-step sandwich immunoassay. Reagents with the following composition are used for the test:

Reagent 1:

0–0.3 μg/ml biotinylaminocaproyl $\overline{\text{NSWGCAFRQVCHTT}}$ (peptide 1, prepared according to Example 1)
40 mmol/l phosphate buffer pH 7.0
0.9% by weight sodium chloride
10% by volume bovine serum albumin Reagent 2:

20 mU/ml of a conjugate of peroxidase and a polyclonal sheep antibody to human immunoglobulin
40 mmol/l phosphate buffer pH 7.0
0.05% by weight Tween 20
0.2% bovine serum albumin
0.2% bovine IgG 1 ml of Reagent 1 and 10 ul sample are incubated at room temperature in a polystyrene tube coated with streptavidin (prepared according to Example 1 of U.S. Ser. No. 356,336, referred to supra). Afterwards it is washed three times with tap water, incubated with 1 ml Reagent 2 for one hour at room temperature and washed again three times with tap water. For the test reaction 1 ml ABTS ®. (2,2'-azino-di[3-ethyl- benzthiazoline-sulfonic acid (6)]-diammonium salt) in 100 mmol/l phosphate citrate buffer pH 4.4 containing 3.2 mmol/l sodium perborate is added. After 60 min the absorbance at 422 nm is measured photometrically. The following results were obtained for the different concentrations of peptide 1:

| Concentration peptide 1 | Absorbance at 422 nm |
|---|---|
| 0 μg/ml | 120 mA |
| 0.002 μg/ml | 240 mA |
| 0.005 μg/ml | 690 mA |
| 0.01 μg/ml | 1150 mA |
| 0.04 μg/ml | 1570 mA |
| 0.07 μg/ml | 1570 mA |
| 0.1 μg/ml | 1570 mA |
| 0.3 μg/ml | 1330 mA |

It will be understood that the specification and examples are illustrative but not limitative of the present invention and that other embodiments within the spirit and scope of the invention will suggest themselves to those skilled in the art.

We claim:

1. Method for determining antibodies against human immunodeficiency virus, comprising:
   (a) incubating a sample with
      (i) a reaction vessel having streptavidin bound thereto at a concentration of from about 0.1 μg/ml to about 2.5 μg/ml of the volume of said reaction vessel,
      (ii) at least one biotinylated polypeptide consisting of from 7 to 50 amino acids and containing at least one amino acid sequence selected from the group consisting of $\overline{\text{CAFROVC}}$ and $\overline{\text{CSGKLIC}},$ and
      (iii) a labelled receptor which specifically binds to an HIV specific antibody, under conditions favoring formation of complexes containing biotinylated polypeptide HIV specific antibody and labelled HIV antibody receptor with said bound streptavidin;
   (b) separating bound complexes from said sample and
   (c) measuring labelled receptor on said bound complex or in said sample as a determination of HIV specific antibody in said sample.

2. Method of claim 1, wherein said biotinylated polypeptide contains amino acid sequence $\overline{\text{CAFRQVC}}.$ 3. Method of claim 1, wherein said biotinylated polypeptide contains amino acid sequence $\overline{\text{CSGKLIC}}.$ 4. Method of claim 1, comprising incubating said sample, reaction vessel, biotinylated polypeptide and labelled receptor simultaneously.

5. Method of claim 1, wherein said labelled receptor specifically binds with an Fcγ portion of human immunoglobulin.

6. Method of claim 1, wherein said HIV specific antibody is an antibody which specifically binds HIV-2.

7. Method of claim 1, comprising adding said biotinylated polypeptide in concentration ranging from about 0.005 μg/ml to about 0.4 μg/ml.

8. Method of claim 7, wherein said biotinylated polypeptide is added in a concentration ranging from about 0.02 μg/ml to about 0.3 μg/ml.

9. Method of claim 1, wherein said biotinylated polypeptide contains from 7 to 35 amino acids.

10. Method of claim 1, wherein said biotinylated polypeptide contains from 7 to 20 amino acids.

11. Method of claim 1, wherein said biotinylated polypeptide contains amino acids sequences

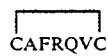
CAFRQVC and

CSGKLIC.

12. Method of claim 1, wherein said labelled receptor is an antibody.

13. Method of claim 1, wherein said biotinylated polypeptide comprises sequence:

X—U—NSWGCAFRQVCHTT or

NSWGCAFRQVCH—B—J wherein
X is a biotinylaminocaproic acid, biotinylaminobutyric acid, biotinyl, N-epsilon-biotinyllysine, N-epsilon(biotinyaminocaproyl)lysine, N-deltabiotinylornithine or N-delta(biotinylaminocaproyl)ornithine residue;
J is an N-epsilon- biotinyllysine, N-epsilon(biotinylaminocapropyl)lysine, N-delta-biotinylornithine or N-delta(biotinylaminocaproyl)-ornithine residue;
U is a bond, L, QARL, ARL, or RL; and
B is a bond, T, TTVPW, TTVP, TTV, or TT.

14. Method of claim 1, wherein said labelled receptor is a polypeptide of from 7 to 50 amino acids and contains at least one amino acid sequence selected from the group consisting of:

CAFRQVC and

CSGKLIC.

15. Method of claim 14, wherein said polypeptide contains amino acids sequence

CSGKLIC.

16. Method of claim 14, wherein said polypeptide contains amino acid sequence

CAFRQVC.

17. Biotinylated polypeptide of the formula:

X—U—NSWGCAFRQVCHTT or

NSWGCAFRQVCH—B—J wherein
X is a biotinylaminocaproic acid, biotinylaminobutyric acid, biotinyl, N-epsilon-biotinyllysine, N-epsilon(biotinyaminocaproyl)lysine, N-deltabiotinylornithine or N-delta(biotinylaminocaproyl)ornithine residue;
J is an N-epsilon biotinyllsine, N-epsilon(biotinylaminocaproyl)lysine, N-delta-biotinylornithine or N-delta(biotinylaminocaproyl)-ornithine residue;
U is a bond, L, QARL, ARL, or RL, and
B is a bond, T, TTVPW, TTVP, TTV or TT.

* * * * *

UNITED STATES PATENT AND TRADEMARK OFFICE
CERTIFICATE OF CORRECTION

PATENT NO. : 5,001,049
DATED : March 19, 1991
INVENTOR(S) : Christian Klein et al.

It is certified that error appears in the above-identified patent and that said Letters Patent is hereby corrected as shown below:

Column 2, line 44: change "amino acid I" to -- amino acid L --.

Column 4, line 25: change "CAFRZVC" to -- CAFRQVC --.

Column 6, line 33 (claim 1): change "CAFROVC" to -- CAFRQVC --.

Title Page:
In the Abstract, line 11: change "CAFROVC" to -- CAFRQVC --.

Signed and Sealed this

Eighth Day of December, 1992

Attest:

DOUGLAS B. COMER

Attesting Officer        Acting Commissioner of Patents and Trademarks